United States Patent [19]

Schefczik et al.

[11] Patent Number: 5,703,238

[45] Date of Patent: Dec. 30, 1997

[54] PREPARATION OF PYRIDINE DYES

[75] Inventors: Ernst Schefczik, Ludwigshafen; Sabine Grüttner-Merten, Bensheim; Peter Saling, Neustadt; Rüdiger Sens, Mannheim; Helmut Reichelt, Neustadt, all of Germany

[73] Assignee: BASF Aktiengesellschaft, Ludwigshafen, Germany

[21] Appl. No.: 682,626

[22] PCT Filed: Jan. 31, 1995

[86] PCT No.: PCT/EP95/00327

§ 371 Date: Jul. 30, 1996

§ 102(e) Date: Jul. 30, 1996

[87] PCT Pub. No.: WO95/21219

PCT Pub. Date: Aug. 10, 1995

[30] Foreign Application Priority Data

Feb. 2, 1994 [DE] Germany .................. 44 02 083.5

[51] Int. Cl.[6] ................... C07D 471/04; C09B 55/00; C09B 25/04

[52] U.S. Cl. ......................................... 546/119; 546/120

[58] Field of Search ........................... 546/119, 120

[56] References Cited

U.S. PATENT DOCUMENTS

| | | | |
|---|---|---|---|
| 4,908,437 | 3/1990 | Hansen | 534/734 |
| 5,079,365 | 1/1992 | Sens et al. | 546/119 |
| 5,101,028 | 3/1992 | Schefczik | 544/127 |
| 5,105,028 | 4/1992 | Dufour et al. | 568/840 |

FOREIGN PATENT DOCUMENTS

| | | |
|---|---|---|
| 0413226 | 2/1991 | European Pat. Off. . |
| 0416434 | 3/1991 | European Pat. Off. . |
| 1292454 | 10/1972 | United Kingdom . |
| 2 001 094 | 1/1979 | United Kingdom . |
| 2014598 | 8/1979 | United Kingdom . |
| WO92/19684 | 11/1992 | WIPO . |

*Primary Examiner*—C. Warren Ivy
*Assistant Examiner*—Evelyn Huang
*Attorney, Agent, or Firm*—Oblon, Spivak, McClelland, Maier & Neustadt, P.C.

[57] ABSTRACT

Methine or azamethine dyes are prepared on the basis of pyridine dyes by condensing an oxime- or formyl-pyridine or its tautomeric form with 5-membered aromatic heterocycles.

11 Claims, No Drawings

PREPARATION OF PYRIDINE DYES

This application is the national phase of PCT/EP 95/00327 filed Jan. 31, 1995.

The present invention relates to a novel process for preparing methine or azamethine dyes on the basis of pyridine dyes by condensing an oxime- or formyl-pyridine or its tautomeric form with 5-membered aromatic heterocycles.

U.S. Pat. No. 5,079,365 discloses triazolopyridine dyes containing 5-membered aromatic heterocyclic radicals attached to the triazolopyridine via a nitrogen atom. Their preparation is effected by condensing the nitrosated heterocycle with the triazolopyridine.

GB-A-2 014 598 describes the condensation of a nitrosopyridone with a pyrazolone.

It is an object of the present invention to provide a novel process for preparing pyridine dyes in a simple manner and in good yield and purity.

We have found that this object is advantageously achieved by a process for preparing pyridine dyes of the formula I

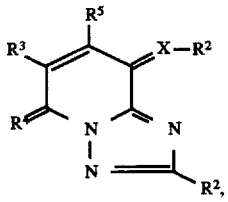

where

X is nitrogen or CH, $R^1$ is $C_1$–$C_{20}$-alkyl, which may be substituted and may be interrupted by one or more oxygen atoms in ether function, substituted or unsubstituted phenyl, or hydroxyl, $R^2$ is a 5-membered aromatic heterocyclic radical, $R^3$ is hydrogen, cyano, carbamoyl, carboxyl or $C_1$–$C_4$-alkoxycarbonyl, $R^4$ is oxygen or a radical of the formula $C(CN)_2$, $C(CN)COOL^1$ or $C(COOL^1)_2$, where $L^1$ is in either case $C_1$–$C_8$-alkyl, which may be interrupted by 1 or 2 oxygen atoms in ether function, and $R^5$ is hydrogen or $C_1$–$C_4$-alkyl, which comprises condensing a pyridine compound of the formula II

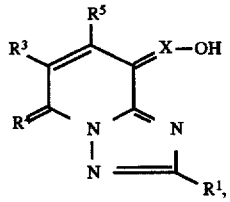

where X, $R^1$, $R^3$, $R^4$ and $R^5$ are each as defined above, with a 5-membered aromatic heterocycle of the formula III

 (III), where $R^2$ is as defined above, in an acid reaction medium at from −10° to +100° C.

The dyes of the formula I can exist in a plurality of tautomeric forms, which are all encompassed by the claims. For example, the compounds of the formula I where $R^4$=oxygen and $R^5$=methyl can exist inter alia in the following tautomeric forms:

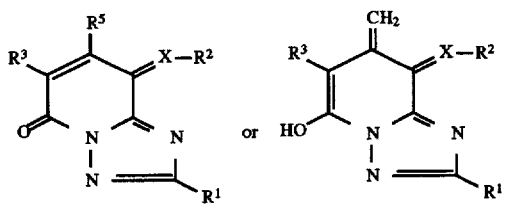

The same is true of the pyridine compounds of formula II. For example, the compounds of the formula II where $R^4$=oxygen can exist inter alia in the following tautomeric forms:

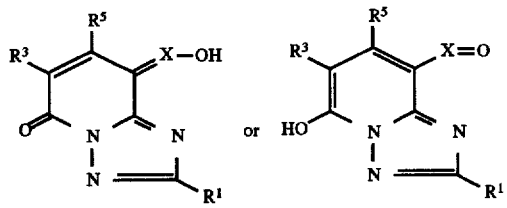

Any substituted alkyl appearing in the abovementioned formulae may for example have as substituents, unless otherwise mentioned, phenyl, $C_1$–$C_4$-alkylphenyl, $C_1$–$C_4$-alkoxyphenyl, halophenyl, $C_1$–$C_8$-alkanoyloxy, $C_1$–$C_8$-alkylaminocarbonyloxy, $C_1$–$C_{20}$-alkoxycarbonyl, $C_1$–$C_{20}$-alkoxycarbonyloxy, and in the last two the alkyl chain may be interrupted by from 1 to 4 oxygen atoms in ether function and/or may be phenyl- or phenoxy-substituted, halogen, hydroxyl or cyano. The number of substituents in substituted alkyl is generally 1 or 2.

In any alkyl appearing in the abovementioned formulae with interruption by oxygen atoms in ether function, the number of oxygen atoms in ether function is preferably, unless otherwise stated, from 1 to 4 in particular 1 or 2.

Any substituted phenyl appearing in the abovementioned formulae may for example have as substituents, unless otherwise stated, $C_1$–$C_8$-alkyl, $C_1$–$C_8$-alkoxy, halogen, in particular chlorine or bromine, or carboxyl. The number of substituents in substituted phenyl is generally from 1 to 3.

$R^2$ can be derived for example from components of the pyrrole, thiazole, thiophene or indole series.

Important radicals $R^2$ are for example those of the formulae IIIa to IIId

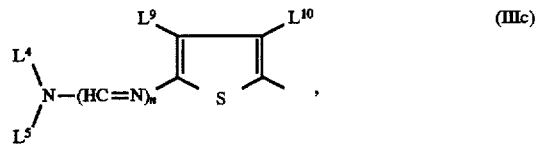

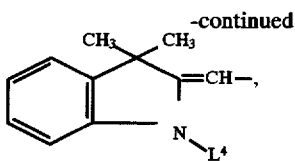

(IId)

where n is 0 or 1,

L⁴ and L⁵ are identical or different and each is independently of the other hydrogen or else with the exception of hydroxyl the abovementioned radical R¹ or together with the nitrogen atom bonding them together a 5- or 6-membered saturated heterocyclic radical with or without further hetero atoms, L⁶ is hydrogen, halogen, $C_1$–$C_8$-alkyl, substituted or unsubstituted phenyl, substituted or unsubstituted benzyl, cyclohexyl, thienyl, hydroxyl or mono-$C_1$–$C_8$-alkylamino, L⁷ and L⁸ are each independently of the other hydrogen, hydroxyl, unsubstituted or phenyl- or $C_1$–$C_4$-alkylphenyl-substituted $C_1$–$C_8$-alkyl, unsubstituted or phenyl- or $C_1$–$C_4$-alkylphenyl-substituted $C_1$–$C_8$-alkoxy, $C_1$–$C_8$-alkanoylamino, $C_1$–$C_8$-alkylsulfonylamino or $C_1$–$C_8$ mono- or dialkylaminosulfonylamino, L⁹ is cyano, carbamoyl, mono- or di($C_1$–$C_8$-alkyl)carbamoyl, $C_1$–$C_8$-alkoxycarbonyl or substituted or unsubstituted phenyl, and L¹⁰ is halogen, hydrogen, $C_1$–$C_4$-alkyl, $C_1$–$C_4$-alkoxy, $C_1$–$C_4$-alkylthio, substituted or unsubstituted phenyl or thienyl.

Any alkyl-appearing in the abovementioned formulae may be straight-chain or branched.

Suitable R¹, R⁵, L¹, L², L³, L⁴, L⁵, L⁶, L⁷, L⁸ and L¹⁰ are each for example, methyl, ethyl, propyl, isopropyl, butyl, isobutyl, sec-butyl or tert-butyl.

R¹, L¹, L², L³, L⁴, L⁵, L⁶, L⁷ and L⁸ may each also be for example pentyl, isopentyl, neopentyl, tert-pentyl, hexyl, 2-methylpentyl, heptyl, 1-ethylpentyl, octyl, 2-ethylhexyl or isooctyl.

R¹, L² and L³ may each also be for example nonyl, isononyl, decyl, isodecyl, undecyl or dodecyl.

R¹ may also be for example tridecyl, isotridecyl, tetradecyl, pentadecyl, hexadecyl, heptadecyl, octadecyl, nonadecyl, eicosyl (the above designations isooctyl, isononyl, isodecyl and isotridecyl are trivial names derived from the oxo process alcohols-cf. Ullmanns Encyklopädie der technischen Chemie, 4th edition, Volume 7, pages 215 to 217, and Volume 11, pages 435 and 436), 2-carboxyethyl, 2-methoxycarbonylethyl, benzyl, 1- or 2-phenylethyl, 3-benzyloxypropyl, phenoxymethyl, 6-phenoxy-4-oxahexyl or 8-phenoxy-4-oxaoctyl.

R¹ and L¹ may each also be for example 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl or 4,8-dioxadecyl.

R¹ may also be for example 3,6,9-trioxadecyl, 3,6,9-trioxaundecyl, 3,6,9-trioxadodecyl, 3,6,9,12-tetraoxatridecyl, 3,6,9,12-tetraoxatetradecyl, 11-oxahexadecyl, 13-butyl-11-oxaheptadecyl or 4,11-dioxapentadecyl.

R³, L², L³ and L⁹ are each for example methoxycarbonyl, ethoxycarbonyl, propoxycarbonyl, isopropoxycarbonyl, butoxycarbonyl, isobutoxycarbonyl or sec-butoxycarbonyl.

L⁹ may also be for example mono- or dimethylcarbamoyl, mono- or diethylcarbamoyl, mono- or dipropylcarbamoyl, mono- or diisopropylcarbamoyl, mono- or dibutylcarbamoyl or N-methyl-N-butylcarbamoyl.

L⁷, L⁸ and L¹⁰ may each also be for example methoxy, ethoxy, propoxy, isopropoxy, butoxy, isobutoxy or sec-butoxy.

L¹⁰ may also be for example methylthio, ethylthio, propylthio, isopropylthio, butylthio, isobutylthio or sec-butylthio.

R¹, L², L³, L⁶ and L¹⁰ may each also be for example phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2,4-dimethylphenyl, 2-, 3- or 4-methoxyphenyl, 2-, 3- or 4-ethoxyphenyl, 2-, 3- or 4-isobutoxyphenyl, 2,4-dimethoxyphenyl, 2-, 3- or 4-chlorophenyl or 2-, 3- or 4-carboxyphenyl.

R¹, L² and L³ may each also be for example 2-hydroxyethyl, 2- or 3-hydroxypropyl, 2-cyanoethyl, 2- or 3-cyanopropyl, 2-acetyloxyethyl, 2- or 3-acetyloxypropyl, 2-isobutyryloxyethyl, 2- or 3-isobutyryloxypropyl, 2-methoxycarbonylethyl, 2- or 3-methoxycarbonylpropyl, 2-ethoxycarbonylethyl, 2- or 3-ethoxycarbonylpropyl, 2-methoxycarbonyloxyethyl, 2- or 3-methoxycarbonyloxypropyl, 2-ethoxycarbonyloxyethyl, 2- or 3-ethoxycarbonyloxypropyl, 2-butoxycarbonyloxyethyl, 2- or 3-butoxycarbonyloxypropyl, 2-(2-phenylethoxycarbonyloxy)ethyl, 2- or 3-(2-phenylethoxycarbonyloxy)propyl, 2-(2-ethoxyethoxycarbonyloxy)ethyl or 2- or 3-(2-ethoxyethoxycarbonyloxy)propyl.

L² and L³ may each also be for example pyridyl, 2-, 3- or 4-methylpyridyl, 2-, 3- or 4-methoxypyridyl, formyl, acetyl, propionyl, butyryl, isobutyryl, pentanoyl, hexanoyl, heptanoyl, octanoyl, 2-ethylhexanoyl, methylsulfonyl, ethylsulfonyl, propylsulfonyl, isopropylsulfonyl, butylsulfonyl, cyclopentylsulfonyl, cyclohexylsulfonyl, cycloheptylsulfonyl, phenylsulfonyl, tolylsulfonyl, pyridylsulfonyl, benzoyl, 2-, 3- or 4-methylbenzoyl, 2-, 3- or 4-methoxybenzoyl, thien-2-ylcarbonyl, thien-3-ylcarbonyl, cyclopentyl, cyclohexyl or cycloheptyl.

L⁶ and L¹⁰ may each also be for example fluorine, chlorine or bromine.

L⁷ and L⁸ may each also be for example formylamino, acetylamino, propionylamino, butyrylamino, methylsulfonylamino, ethylsulfonylamino, propylsulfonylamino, isopropylsulfonylamino, butylsulfonylamino, mono- or dimethylaminosulfonylamino or mono- or diethylaminosulfonylamino.

L² and L³ or L⁴ and L⁵ combined with the nitrogen atom joining them together to form a five- or six-membered saturated heterocyclic radical which may contain further hetero atoms can be for example pyrrolidinyl, piperidinyl, morpholinyl, piperazinyl or N-($C_1$–$C_4$-alkyl)piperazinyl.

Preference is given to the preparation of pyridine dyes of the formula I where R⁵ is methyl.

Preference is further given to the preparation of pyridine dyes of the formula I where R³ is cyano.

Preference is further given to the preparation of pyridine dyes of the formula I where R⁴ is oxygen.

Preference is further given to the preparation of pyridine dyes of the formula I where X is nitrogen.

Preference is further given to the preparation of pyridine dyes of the formula I where R² is derived from a component of the pyrrole, thiazole or thiophene series.

Preference is further given to the preparation of pyridine dyes of the formula I where R¹ or R⁶ is $C_1$–$C_{12}$-alkyl, which may be substituted by $C_1$–$C_6$-alkanoyloxy, $C_1$–$C_8$-alkoxycarbonyl, whose alkyl chain may each be interrupted by 1 or 2 oxygen atoms in ether function, phenyl or $C_1$–$C_4$-alkylphenyl and may be interrupted by 1 or 2 oxygen atoms in ether function.

Particular preference is given to the preparation of pyridine dyes of the formula I where $R^1$ or $R^6$ is alkyl, alkoxyalkyl, alkanoyloxyalkyl or alkoxycarbonylalkyl, each of which has up to 12 carbon atoms, unsubstituted or methyl-substituted benzyl or unsubstituted or methyl-substituted phenyl.

Particular preference is further given to the preparation of pyridine dyes of the formula I where $R^2$ is a radical of the abovementioned formula IIIa or IIIc, in particular IIIa, where $L^4$ and $L^5$ are each independently of the other alkyl, alkoxyalkyl, alkanoyloxyalkyl or alkoxycarbonylalkyl, which may each have up to 12 carbon atoms, hydrogen, unsubstituted or methyl-substituted benzyl or unsubstituted or methyl-substituted phenyl, $L^6$ is hydrogen, $C_1$–$C_4$-alkyl, unsubstituted or $C_1$–$C_4$-alkyl- or $C_1$–$C_4$-alkoxy-substituted phenyl, benzyl or thienyl, $L^9$ is cyano, $L^{10}$ is halogen, hydrogen, $C_1$–$C_4$-alkyl, $C_1$–$C_4$-alkoxy, $C_1$–$C_4$-alkylthio, unsubstituted or $C_1$–$C_4$-alkyl-substituted phenyl or thienyl, and n is 0.

The pyridine compounds of the formula II and the heterocycles of the formula III can be used in the process of the invention in a molar ratio ranging from 1:2 to 2:1, preferably from 1.4:1 to 1.5:1.

The novel process is generally carried out at atmospheric pressure and at a temperature from $-10°$ to $+100°$ C., preferably from $20°$ to $80°$ C., in particular from $30°$ to $70°$ C., the range from $55°$ to $65°$ C. being particularly suitable, in an acid reaction medium.

Suitable acid reaction media include for example aqueous acids, water-containing alcoholic acids, alcoholic acids or acetic anhydride.

Aqueous acids include for example dilute acids which have a pH from 0 to 5, preferably from 1 to 3, in particular about 2. Suitable examples are dilute hydrochloric acid, dilute sulfuric acid or mixtures thereof together with acetic acid.

If water-containing or water-free alcoholic acids are used, suitable alcohols include in particular $C_1$–$C_4$-alkanols, such as methanol, ethanol, propanol, isopropanol, butanol, isobutanol, sec-butanol or tert-butanol.

Suitable water-containing alcoholic acids include in particular mixtures (from 1:20 to 20:1 v/v) of the abovementioned aqueous acids with the alcohols mentioned.

Alcoholic acids for the purposes of the present invention are in particular semisaturated to saturated solutions of hydrogen chloride in the alcohols mentioned or else mixtures of polyphosphoric acid and alcohols.

Based on the weight of the reactants (pyridine compound II and heterocycle III) the acid reaction medium is generally used in an amount from 10 to 40% by weight, preferably from 20 to 25% by weight.

The novel process, which can be carried out continuously as well as batchwise, is advantageously carried out by initially charging the pyridine compound of the formula II in the acid reaction medium and adding the heterocycle III at the temperature according to the invention. Following a subsequent stirring phase, which generally takes from 0.5 to 2 hours and is carried out at the temperature according to the invention, the reaction will have ended, and it is then possible to isolate the target products in a conventional manner.

This can be done for example by direct phase separation or by taking up the reaction product in a suitable organic solvent, eg. toluene or xylene, after which, in the second case, the aqueous phase is separated off and the pyridine dye of the formula I is precipitated from the organic phase, for example by addition of methanol.

It is also possible to purify the reaction mixture by passing it through silica gel or alumina.

A particularly preferred version of the process according to the invention is to prepare the pyridine dyes of the formula I where X is nitrogen in a one-pot process. The first step in this process is to treat a pyridine of formula IV

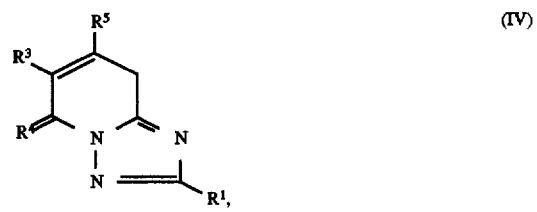

(IV)

where $R^1$, $R^3$, $R^4$ and $R^5$ are each as defined above, with a nitrosating agent, for example with from 5 to 40% strength by weight aqueous sodium nitrite solution, solid sodium nitrite or neopentylglycol dinitrite, at from $-10°$ to $+35°$ C., preferably from $0°$ to $20°$ C., in an aqueous acid reaction medium, for example in concentrated hydrochloric acid, in the presence or absence of acetic acid, or in an alcoholic acid reaction medium, for example in a mixture of polyphosphoric acid and an alcohol, to convert it into the pyridine compound of the formula II (X=N). The resulting reaction mixture is then, if necessary after dilution with acid reaction medium, admixed with the heterocycle III and further processed as described above.

The pyridine compounds of the formula II are known per se and are described for example in U.S. Pat. No. 5,105,028 or can be obtained by the methods mentioned therein or else mentioned in the Examples which follow.

The novel process supplies the pyridine dyes of the formula I in a simple manner and in good yield and purity. A particular advantage of the process according to the invention is that azamethine dyes are prepared without the use of nitrosated compounds derived from heterocycles of the formula III, since these frequently lack stability and give low product yields and, what is more, are difficult to handle. This applies particularly to 4-alkylthiazoles.

As mentioned earlier, the pyridine dyes of the formula I are useful dyes for the thermal dye transfer process.

The Examples which follow illustrate the invention.

EXAMPLE 1

To a solution of 272 g (1 mol) of the triazolopyridone of the formula

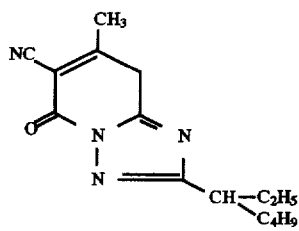

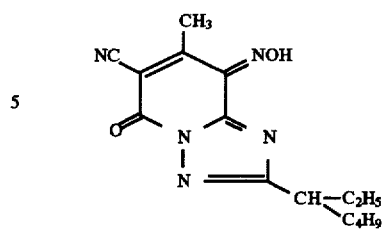

in 1,400 ml of glacial acetic acid and 1,400 ml of concentrated hydrochloric acid was added, after 30 minutes stirring, 600 ml of 23% strength by weight aqueous sodium nitrite solution at from 0° to 5° C. over 1 h and the mixture was subsequently stirred at from 0° to 10° C. for 2 h. Then 1 l of water was added. At from 10° to 20° C. were then added 230 g (0.8 mol) of 2-dibutylamino-4-phenylthiazole and the mixture was subsequently stirred at from 15° to 20° C. for 30 min. Then 10 g of amidosulfuric acid were added and the suspension was subsequently stirred at from 15° to 20° C. for 20 min. A total of 800 ml of concentrated sodium hydroxide solution was used to set a pH of 2. In the process the suspension dissolved to form a bluish green solution. It was subsequently stirred at 30° C. for 30 min, heated to 60° C. and stirred at that temperature for 2 h. The flask contents were subsequently cooled down to 0°–5° C. A greasy tacky product formed and was taken up in 400 ml of toluene. The aqueous phase was separated off, toluene was distilled off, and 1,000 ml of methanol were added in the heat. The mixture was then cooled down to 0°–10° C., and the precipitated dye was filtered off with suction and washed with a little methanol and water. Drying at 60° C. under reduced pressure yielded 233 g (51%) of the dye of the formula

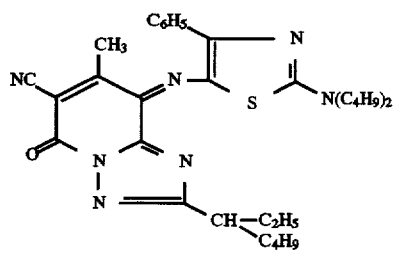

(Purity: >98%; mp. 146°–148° C.)

EXAMPLE 2

Example 1 was repeated without amidosulfuric acid, affording 260 g (57%) of dye.

EXAMPLE 3

Example 1 was repeated without the addition of toluene; instead, the 2 h of stirring at 60° C. was followed by direct separation of the phases at 50° C. Thereafter the organic phase was mixed with 200 ml of methanol, and the dye precipitated and was separated off. Yield: 233 g (51%).

EXAMPLE 4 a) Example 1 was repeated with the difference that, after the treatment with sodium nitrite had been carried out, the compound of the formula was isolated by filtering off with suction, washing and drying. The yield of this compound was 241 g (80%).

b) To carry out the condensation, 301 g (1 mol) of the compound described under a) were dissolved in a mixture of 600 ml of isopropanol and 100 g of polyphosphoric acid and admixed with 288 g (1 mol) of 2-dibutylamino-4-phenylthiazole. The mixture was subsequently stirred at 60° C. for 2 h and then worked up in the manner of Example 1. 371 g (65%) were obtained of the dye.

EXAMPLE 5

To a solution in 250 ml of chloroform of 272 g (1 mol) of the triazolopyridone used as starting material in Example 1 were added 120 g of N,N-dimethylformamide and 252 g (1 mol) of phosphoryl chloride. The batch was subsequently refluxed for 6 h, after which 250 ml of water were added with care, and the mixture was subsequently stirred at room temperature for 30 min. After the water had been separated off, the organic phase was admixed with 180 g of acetic anhydride. Then 345 g (1.2 mol) of 2-dibutylamino-4-phenylthiazole were added dropwise, and thereafter the mixture was heated for 8 h under a water separator. The chloroform was distilled off, and the residue was filtered off with suction and washed with water and a little methanol to leave 186 g (32.5%) of the dye of the formula

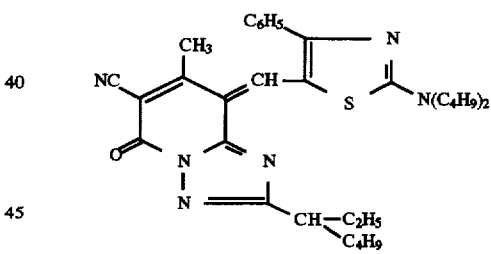

(mp.: 189°–192° C.)

EXAMPLE 6

6 g of the compound of the formula

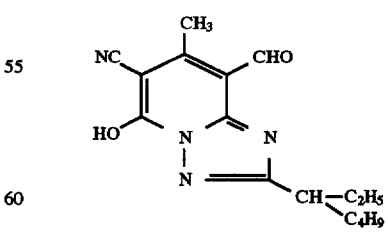

were stirred with 5.1 g of 2-diethylamino-4-phenylthiazole (90.8% strength by weight) in 30 ml of acetic anhydride at 35° C. for 3 h and at 60° C. for 2 h. The solid was filtered off with suction, washed with methanol and water and dried to leave 5.75 g of the dye of the formula

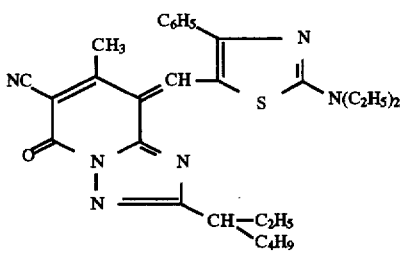

($\lambda_{max}$=561 nm, in DMF; mp.: 205°–206° C.)

The same method gave the dyes listed in the following table:

| Ex. No. | $R^2$ | $\lambda_{max}$ [nm] |
|---|---|---|
| 7 | ![structure with C6H5, N, S, (CH2)2O(CH2)2OCH3, (CH2)3OCH3] | 561 |
| 8 | ![structure with Cl-phenyl, N, S, NHC2H4OCH3] | 563 |

EXAMPLE 9

7.5 g (0.025 mol) of the compound described in Example 4a) and 7.5 g (0.025 mol) of 2-(di-sec-butylamino)-4-tert-butylthiazole were refluxed for 15 min in a mixture of 12 ml of glacial acetic acid and 12 ml of propionic acid. The batch was then cooled down to room temperature and purified over silica gel using 9:1 v/v toluene/ethyl acetate as mobile phase. This yielded 2.63 g (19%) of the dye of the formula

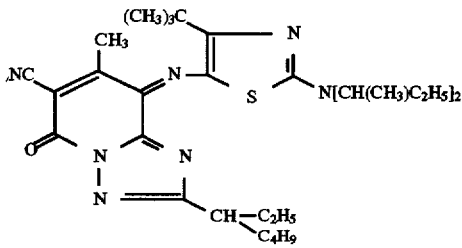

We claim:

1. A process for preparing pyridine dyes having the formula (I):

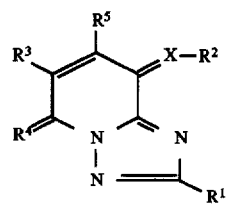

wherein:

X is nitrogen or CH;

$R^1$ is $C_1$–$C_{20}$-alkyl, which is unsubstituted or substituted and which is uninterrupted or interrupted by one or more oxygen atoms in ether function, said substitution being phenyl, $C_1$–$C_4$-alkylphenyl, $C_1$–$C_4$-alkoxyphenyl, halophenyl, $C_1$–$C_8$-alkanoyloxy, $C_1$–$C_8$-alkylaminocarbonyloxy or $C_1$–$C_{20}$-alkoxycarbonyl;

$R^2$ is a 5-membered aromatic heterocyclic radical;

$R^3$ is hydrogen, cyano, carbamoyl, carboxyl or $C_1$–$C_4$-alkoxycarbonyl;

$R^4$ is oxygen or a radical of the formula $C(CN)_2$, $C(CN)COOL^1$ or $C(COOL^1)_2$, where $L^1$ is in either case $C_1$–$C_8$-alkyl, which is uninterrupted or interrupted by one or two oxygen atoms in ether function; and $R^5$ is hydrogen or $C_1$–$C_4$-alkyl; which comprises condensing a pyridine compound of the formula (II):

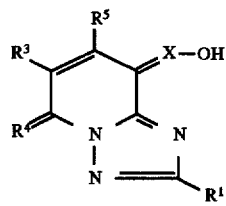

wherein X, $R^1$, $R^3$, $R^4$ and $R^5$ are each as defined above, with a 5-membered aromatic heterocycle of the formula (III):

$R^2$—H(III), wherein $R^2$ is as defined above, in an acid reaction medium at a pH of from about 0 to about 5 at from about −10° to +100° C.

2. The process of claim 1, wherein $R^5$ is methyl.

3. The process of claim 1, wherein $R^3$ is cyano.

4. The process of claim 1, wherein $R^4$ is oxygen.

5. The process of claim 1, wherein X is nitrogen.

6. The process of claim 1, wherein $R^2$ is a radical of pyrrole, thiazole, thiophene or indole series.

7. The process of claim 1, wherein the condensation is carried out at from about 20° to 80° C.

8. The process of claim 1, wherein $R^2$ is selected from the group consisting of

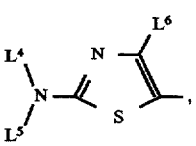

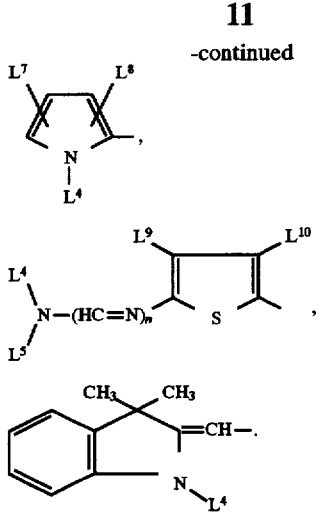

wherein:

n is 0 or 1, $L^4$ and $L^5$ are indentical or different and each is independently of the other hydrogen or else with the exception of hydroxyl the abovementioned radical $R^1$ or together with the nitrogen atom bonding them together a 5- or 6-membered saturated heterocyclic radical with or without further hetero atoms, $L^6$ is hydrogen, halogen, $C_1$-$C_8$-alkyl, substituted or unsubstituted phenyl, substituted or unsubstituted benzyl, cyclohexyl, thienyl, hydroxyl or mono-$C_1$-$C_8$-alkylamino, $L^7$ and $L^8$ are each independently of the other hydrogen, hydroxyl, unsubstituted or phenyl- or $C_1$-$C_4$-alkylphenyl-substituted $C_1$-$C_8$-alkyl, unsubstituted or phenyl- or $C_1$-$C_4$-alkylphenyl-substituted $C_1$-$C_8$-alkoxy, $C_1$-$C_8$-alkanoylamino, $C_1$-$C_8$-alkylsulfonylamino or $C_1$-$C_8$-mono- or dialkylaminosulfonylamino, $L^9$ is cyano, carbamoyl, mono- or di($C_1$-$C_8$-alkyl)carbamoyl, $C_1$-$C_8$-alkoxycarbonyl or substituted or unsubstituted phenyl, and $L^{10}$ is halogen, hydrogen, $C_1$-$C_4$-alkyl, $C_1$-$C_4$-alkoxy, $C_1$-$C_4$-alkylthio, substituted or unsubstituted phenyl or thienyl.

9. The process of claim 7, wherein the condensation is carried out at from 30° to 70° C.

10. The process of claim 1, wherein the condensation is carried out at a pH of from about 1 to 3.

11. The process of claim 10, wherein the condensation is carried out at a pH of about 2.

* * * * *

UNITED STATES PATENT AND TRADEMARK OFFICE
CERTIFICATE OF CORRECTION

PATENT NO. : 5,703,238
DATED : December 30, 1997
INVENTOR(S) : Ernst SCHEFCZIK et al.

It is certified that error appears in the above-indentified patent and that said Letters Patent is hereby corrected as shown below:

On the Title page, Item [30], the Foreign Application Data should read:

-- Feb. 2, 1994    [DE]    Germany ....... 44 03 083.5 --

Signed and Sealed this

Fifth Day of May, 1998

*Attest:*

*Attesting Officer*

BRUCE LEHMAN
*Commissioner of Patents and Trademarks*